United States Patent [19]
Hyodo et al.

[11] Patent Number: 5,260,289
[45] Date of Patent: Nov. 9, 1993

[54] COMPOSITION FOR TREATING PAIN, METHOD FOR TREATING PAIN AND COMPOSITION FOR REINFORCING PAIN RELIEF ACTION

[75] Inventors: Masayoshi Hyodo, Takatsuki; Masataka Akiyoshi, Ashiya, both of Japan

[73] Assignee: Vitacain Pharmaceutical Co., Ltd., Osaka

[21] Appl. No.: 898,032

[22] Filed: Jun. 12, 1992

[51] Int. Cl.$^5$ ..................... A61K 31/62; A61K 31/59
[52] U.S. Cl. ..................................... 514/161; 514/167
[58] Field of Search ............................... 514/161, 167

Primary Examiner—S. J. Friedman

[57] ABSTRACT

A composition for treating pain, which contains dibucaine, a pharmaceutically acceptable salt of salicylic acid, calcium bromide, and antiphlogistic steroid(s) as active ingredients; and a method for reducing pain, which comprises injecting said composition into the location of pain. Further, the present invention provides a composition containing antiphlogistic steroid as an active ingredient, which is for reinforcing pain relief action of a composition containing dibucaine, a pharmaceutically acceptable salt of salicylic acid, and calcium bromide; and a novel use of antiphlogistic steroid in the treatment of pain.

11 Claims, No Drawings

COMPOSITION FOR TREATING PAIN, METHOD FOR TREATING PAIN AND COMPOSITION FOR REINFORCING PAIN RELIEF ACTION

FIELD OF THE INVENTION

The present invention relates to injectable compositions for treating pain, methods for treating pain, and a novel use of antiphlogistic steroids.

BACKGROUND OF THE INVENTION

Conventionally, pain caused by rheumatic diseases and locomotorium diseases has been treated with nonsteroidal antiinflammatory, local anesthetic and antispasmodic which are generally referred to as analgesics in a wide sense, and vasoconstriction, vasodilator and muscular relaxant having other actions as well, which may be used in combination. This treatment using plural medicaments is based on the development mechanisms of pain, and the mechanism of action of medicaments. For example, nonsteroidal antiinflammatory exhibits etiotropic effects by inhibiting synthesis of the pain-producing substance prostaglandins, while local anesthetic exhibits symptomatic effects by blocking transmission of neurostimulation from local pain source to the center, and the combination of these medicaments aims at synergistic effects afforded by their different actions displayed at different sites. An exemplary of the medicaments formulated for achieving such synergistic effects is Neo Vitacain injection ® (VITACAIN PHARMACEUTICAL CO., LTD., Japan), which is a local injection containing dibucaine hydrochloride, sodium salicylate, and calcium bromide as active ingredients and having a formulation shown below, and is markedly effective as an analgesic for use in a pain treatment of head neuralgia, muscle pain, rheumatism, low backache, etc. Usefulness of Neo Vitacain injections ® and its analogous therapeutic compositions for the treatment of pain will be greatly enhanced if the effect thereof could be improved.

| Formulation of Neo Vitacain injection ® (100 ml): | |
| --- | --- |
| Dibucaine hydrochloride | 100 mg |
| Sodium salicylate | 300 mg |
| Calcium bromide | 200 mg |
| Thiamine hydrochloride | 200 mg |
| Pyridoxin hydrochloride | 100 mg |
| Calcium pantothenate | 100 mg |

SUMMARY OF THE INVENTION

An object of the present invention is to provide novel pharmaceutical compositions effective for algetic diseases.

Another object of the present invention is to provide methods for treating algetic diseases.

A still another object of the present invention is to provide a novel use of antiphlogistic steroids as contained in a composition for reinforcing pain relief action, which is used with other analgesic such as Neo Vitacain injection ® for the treatment of pain.

The present inventors have conducted intensive studies with the aim of achieving the above-mentioned purposes, and found that a composition obtained by adding antiphlogistic steroid(s) to a composition containing dibucaine, a pharmaceutically acceptable salt of salicylic acid and calcium bromide has a pain relief effect which is superior to the conventional agents for treating pain, and that said composition is extremely useful for the treatment of pain. Moreover, the present inventors have found that the treatment using a composition containing dibucaine, a pharmaceutically acceptable salt of salicylic acid, calcium bromide and antiphlogistic steroid(s) is an extremely effective method for reducing pain. Still further, the present inventors have found that an antiphlogistic steroid can reinforce pain relief effect of a composition containing dibucaine, a pharmaceutically acceptable salt of salicylic acid, and calcium bromide. With these findings, the present inventors have completed the present invention.

That is, the present invention is:

1. An injectable composition for treating pain, which contains dibucaine, a pharmaceutically acceptable salt of salicylic acid, calcium bromide, and antiphlogistic steroid(s);

2. A method for treating pain, comprising injecting a composition containing dibucaine, a pharmaceutically acceptable salt of salicylic acid, calcium bromide, and antiphlogistic steroid(s), into the location of pain;

3. A composition containing antiphlogistic steroid(s) and pharmaceutically acceptable carriers for reinforcing pain relief action of a composition containing dibucaine, a pharmaceutically acceptable salt of salicylic acid, and calcium bromide; and 4. Use of antiphlogistic steroid(s) as contained in a composition for reinforcing pain relief action of a composition containing dibucaine, a pharmaceutically acceptable salt of salicylic acid, and calcium bromide.

DETAILED DESCRIPTION OF THE INVENTION

The pain here particularly means pain at a local region or site, and includes myofascial pain, eircumomarthritis, symptomatic neuralgia, and transdermal, muscular and articular pain accompanying locomotorium diseases. Specific examples include occipital neuralgia, temporal neuralgia, muscle pain, neuralgia, chronic rheumatism, low backache, backache, pain caused by autonomic nerve sensitivity, migraine, trigeminal pain, frozen shoulder, and pain caused by disorders of autonomic nerve (e.g. algetic insomnia, menopausal neuralgia).

The treatment of pain in this specification means treatments given for the purpose of removing or alleviating the above-mentioned pains.

The dibucaine to be used in the present invention is normally in the form of a salt, with preference given to dibucaine hydrochloride.

The antiphlogistic steroid to be used in the pharmaceutical composition of the present invention may be any antiphlogistic steroid as long as it can be used as an injection, and examples thereof include dexamethasone, betamethasone, methylprednisolone, preunisolone, and salts thereof. These antiphlogistic steroids are normally used in the form of pharmaceutically acceptable salts, and are exemplified by dexamethasone acetate, dexamethasone palmitate, dexamethasone sodium phosphate, dexamethasone sodium metasulfobenzoate, betamethasone acetate, betamethasone sodium phosphate, preunisolone acetate, prednisolone butylacetate, preunisolone sodium succinate, methylprednisolone acetate and methylprednisolone sodium succinate, with preference given to dexamethasone sodium phosphate, betainethasone sodium phosphate, and methylprednisolone acetate.

The pharmaceutically acceptable salt of salicylic acid to be used in the present invention is exemplified by alkali metal salts, and preferred is sodium salt.

The composition for treating pain of the present invention contains each component at a proportion of 100-1000 parts by weight, preferably 200-500 parts by weight of a pharmariceutically acceptable salt of salicylic acid, and 50-500 parts by weight, preferably 100-300 parts by weight of calcium bromide per 100 parts by weight of dibucaine. The proportion of the antiphlogistic steroid varies depending on the kind thereof, and dexamethasone and betamethasone are normally contained in a proportion of 4-80 parts by weight, preferably 6-40 parts by weight, and preunisolone and methylprednisolone are normally contained in a proportion of 80-2000 parts by weight, preferably 100-1000 parts by weight per 100 parts by weight of dibucaine.

In Table 1, the amounts of various antiphlogistic steroids to be added to 5 ml of, for example, Neo Vitacain injection ® are detailedly shown. The amounts shown here are on an antiphlogistic steroid basis, and in practice, they are recalculated into the salt amounts to be preferably used.

TABLE 1

Amounts of various steroids to be added to 5 ml of Neo Vitacain

| Steroid to be added | normal amount (mg) | preferable amount (mg) |
| --- | --- | --- |
| Dexamethasone | 0.2–4.0 | 0.3–2.0 |
| Betamethasone | 0.2–4.0 | 0.3–2.0 |
| Methylprednisolone | 4.0–80.0 | 5.0–40.0 |
| Prednisolone | 5.0–100.0 | 5.0–50.0 |

The composition of the present invention may contain additives normally accepted from the aspect of the formulation of pharmaceutical preparations. For example, carriers, stabilizers (e.g. creatinine), solubilizers (e.g. glycerin), suspending agents (e.g. carboxymethylcellulose), buffers (e.g. citric acid, sodium hydrogencarbonate), emulsifiers (e.g. fatty acid monoglyceride, sorbitan fatty acid ester, polyoxyethylene lauryl ether, etc.), antiseptics (e.g. methyl p-oxybenzoate, propyl p-oxybenzoate, etc.) and antioxidants (e.g. t-butylhydroxyanisole) may be added to liquid compositions, and excipients may be further added to powder compositions.

In the present invention, the aforementioned compositions are preferably injected into the location site of pain, and for this reason, the compositions of the present invention for the treatment of pain may take any form as long as they can be prepared into injections when in use. Examples thereof include aqueous solution, suspension, emulsion, and powders to be dissolved, suspended or emulsified when in use. They may be prepared by conventional methods. The pH of the aqueous solution, suspension, and emulsion is preferably within the range of from pH 4 to 7, particularly preferably at about pH 6, in which a long-term storage can be attained despite the instability of dexamethasone phosphate in the acidic range and instability of dibucaine hydrochloride in the alkali range, and pH of the preparations is adjusted to said range by conventional methods. Also, the powder compositions may be prepared in such a manner as adjusts their pH to be in the range of from 4 to 7, preferably about 6 upon dissolution in sterilized water or sterilized physiological saline.

The composition for the treatment of pain, and the composition for reinforcing pain relief action of the present invention are administered to mammals such as human, dog, cow, horse and cat, particularly to human.

The composition for treating pain and composition for reinforcing pain relief action of the present invention are injected locally, such as into muscle, peritenon and articular cavity.

While the dose of the composition for treating pain of the present invention varies depending on age of patients, symptom, administration site and drugs to be used, taking a therapeutic composition of the above-described formulation wherein antiphlogistic steroid(s) is(are) added to 5 ml of Neo Vitacain injection ® in an amount given in Table 1, as an example, it is normally 0.1–25 ml, preferably 0.5–5 ml per site, namely, 0.1–25 mg, preferably 0.5–5 mg of dibucaine hydrochloride, 0.1–250 mg, preferably 1–25 mg of sodium salicylate, 0.05–125 mg, preferably 0.5–15 mg of calcium bromide, to which 0.004–500 mg of antiphlogistic steroid(s) may be added, wherein 0.004–20 mg, preferably 0.03–2 mg of dexamethasone and/or betamethasone, and/or 0.08–500 mg, preferably 0.5–50 mg of methylprednisolone and/or preunisolone is(are) used as the antiphlogistic steroid(s).

Since the method for treating pain of the present invention permits long-lasting and potent pain treatment effects, intermittent administration can be performed. While administration frequency differs depending on age of patients, symptom and pain location, once or twice a week, or 1 to 4 times in 2 weeks can exert sufficient effects. The method for treating pain of the present invention affords not only superior pain relief effect but also reduced pain at the time of the needle puncture and insertion of a drug.

In the present invention, the composition for reinforcing pain relief action is a general concept embracing those having an action of potentiating pain relief action when added to a compound or composition having pain relief action or when used independently but together with said compound or composition. In the present invention, it means a composition containing, as an active ingredient, antiphlogistic steroid which is capable of additionally reinforcing pain reducing effect possessed by a composition containing dibucaine, a pharmaceutically acceptable salt of salicylic acid and calcium bromide, when added thereto or used independently but together with said composition.

The composition for reinforcing pain relief action of the present invention may be in the form of injectable solutions, suspensions or emulsions, or powders which can be dissolved, suspended or emulsified when in use as an injection.

The aforementioned additives for the composition for treating pain may be also added to the composition for reinforcing pain relief action.

The use of the composition for reinforcing pain relief action may be performed by adding same to an injectable composition containing dibucaine, a pharmaceutically acceptable salt of salicylic acid, and calcium bromide, particularly Neo Vitacain injection ®, or by an independent use thereof together with a composition containing dibucaine, a pharmaceutically acceptable salt of salicylic acid, and calcium bromide when it is used for the treatment of pain.

The composition for reinforcing pain relief action of the present invention is preferably used in admixture with an injectable composition containing dibucaine, a pharmaceutically acceptable salt of salicylic acid, and calcium bromide. The composition for reinforcing pain relief action is added to said composition containing dibucaine, a pharmaceutically acceptable salt of salicylic acid, and calcium bromide in the same amount as that in the aforementioned composition for treating pain, on an antiphlogistic steroid basis. That is, the composition for reinforcing pain relief action is added in an amount of 0.25-800 parts by weight per 100 parts by weight of the total amount of dibucaine, a pharmaceutically acceptable salt of salicylic acid, and calcium bromide, on an antiphlogistic steroid basis.

Each component and the composition containing dibucaine, a pharmaceutically acceptable salt of salicylic acid, and calcium bromide to be used in the present invention have been conventionally used as pharmaceuticals, and safety thereof in the abovementioned administration amounts has been already established. For example, acute toxicity of Neo Vitacain injection ® is shown in $LD_{50}$ of 34 ml/kg, and addition thereto or independent use together therewith of antiphlogistic steroid in an amount mentioned above did not result in significant Increase of toxicity.

| Example 1 (Injection formulation, 100 ml) | |
|---|---|
| Dibucaine hydrochloride | 100 mg |
| Sodium salicylate | 300 mg |
| Calcium bromide | 200 mg |
| Thiamine hydrochloride | 200 mg |
| Pyridoxin hydrochloride | 100 mg |
| Calcium pantothenate | 100 mg |
| Dexamethasone sodium phosphate | 20 mg |
| Example 2 (Injection formulation, 100 ml) | |
| Dibucaine hydrochloride | 100 mg |
| Sodium salicylate | 300 mg |
| Calcium bromide | 200 mg |
| Betamethasone sodium phosphate | 20 mg |
| Example 3 (Injection formulation, 100 ml) | |
| Betamethasone sodium phosphate | 200 mg |
| Sodium sulphite | 30 mg |
| p-Oxybenzoic acid | 75 mg |
| Creatinine | 400 mg |
| Example 4 (Composition for reinforcing pain relief action, Injection formulation, 100 ml) | |
| Methylprednisolone acetate | 2 g |
| Polyethylene glycol | 3 g |

The pain relief action of the composition for treating pain of the present invention, and the reinforcing effect of the composition for reinforcing pain relief action of the present invention on the agents for treating pain are hereinbelow described in detail.

EXPERIMENT 1

To a patient (male, age 63) who had been suffering from myofascial low backache for 2 months was administered the following medicament once a week, and the degree of pain before administration every week was compared.

In evaluating the pain, the initial pain was taken as 10, and the absence of pain was taken as 0, which is the same in the following experiments.
Medicament administered
  A: Neo Vitacain 3 ml
  B: Neo Vitacain 3 ml + Dexamethasone sodium phosphate 0.5 mg
Administration site
  Medicament A: left lumbar region
  Medicament B: right lumbar region
The results are summarized in Table 2, in which it is shown that addition of an antiphlogistic steroid to Neo Vitacain resulted in earlier removal of the pain than the sole use of Neo Vitacain, thereby indicating remarkable potentiation of the effect of pain treatment.

TABLE 2

| | before 1st administration | before 2nd administration | before 3rd administration | before 4th administration | before 5th administration |
|---|---|---|---|---|---|
| Neo Vitacain | 10 | 6 | 4 | 3 | 1 |
| Neo Vitacain + steroid | 10 | 4 | 0 | — | — |

EXPERIMENT 2

To a patient (female, age 27) who had been suffering from tenontothecitis of both thumbs for 3 months was administered the following medicament once a week, and the effect was evaluated as in Experiment 1.
Medicament administered
  A: Neo Vitacain 0.5 ml
  B: Neo Vitacain 0.5 ml + Dexamethasone sodium phosphate 0.1 mg
Administration site
  Medicament A: right thumb
  Medicament B: left thumb
The results are summarized in Table 3, in which it is shown that addition of an antiphlogistic steroid to Neo Vitacain resulted in earlier removal of the pain than the sole use of Neo Vitacain, thereby indicating remarkable potentiation of the effect of pain treatment.

TABLE 3

| | before 1st administration | before 2nd administration | before 3rd administration | before 4th administration |
|---|---|---|---|---|
| Neo Vitacain | 10 | 7 | 5 | 3 |
| Neo Vitacain + steroid | 10 | 3 | 0 | — |

EXPERIMENT 3

To a patient (male, age 46) who had been suffering from myofascial pain (tenchu syndrome) at the nuchal region for 1 month was administered the following medicament particularly at the tenchu part of the right and left nuchal regions, and the effects were evaluated as in Example 1.
Medicament administered
  A: Neo Vitacain 2 ml
  B: Neo Vitacain 2 ml + Methylprednisolone acetate 4 mg
Administration site
  Medicament A: left nuchal region
  Medicament B: right nuchal region
The results are summarized in Table 4, in which it is shown that addition of an antiphlogistic steroid to Neo Vitacain resulted in earlier removal of the pain than the sole use of Neo Vitacain, thereby indicating remarkable potentiation of the effect of pain treatment.

TABLE 4

| | before 1st administration | before 2nd administration | before 3rd administration | before 4th administration | before 5th administration |
|---|---|---|---|---|---|
| Neo Vitacain | 10 | 7 | 5 | 4 | 4 |
| Neo Vitacain + | 10 | 4 | 2 | 2 | 0 |

TABLE 4-continued

| | before 1st administration | before 2nd administration | before 3rd administration | before 4th administration | before 5th administration |
|---|---|---|---|---|---|
| steroid | | | | | |

What is claimed is:

1. An injectable composition for treating pain, which comprises 100 parts by weight of dibucaine, 100–1,000 parts by weight of a pharmaceutically acceptable salt of salicyclic acid, 50–500 parts by weight of calcium bromide, and 4–500 parts by weight of antiphlogistic steroid(s).

2. A composition for treating pain according to claim 1, which is a liquid having a pH in the range of from 4 to 7.

3. A composition for treating pain, which comprises 0.1–25 mg of dibucaine hydrochloride, 0.1–250 mg of a pharmaceutically acceptable salt of salicylic acid, 0.05–125 mg of calcium bromide, and 0.004–500 mg of antiphlogistic steroid(s).

4. A composition for treating pain according to claim 1, 2 or 3, wherein the antiphlogistic steroid is at least one member selected from the group consisting of dexamethansone, betamethansone, methylprednisolone, prednisolone and their pharmaceutically acceptable salts.

5. A composition for reinforcing pain relief action according to claim 1, wherein the antiphlogistic steroid is at least one member selected from the group consisting of dexamethasone, betamethasone, methylprednisolone, prednisolone and their pharmaceutically acceptable salts.

6. A method for treating pain, characterized by injecting a composition containing dibucaine, a pharmaceutically acceptable salt of salicyclic acid, calcium bromide, and antiphlogistic steroid(s) into the location of pain.

7. A method for treating pain according to claim 6, wherein the composition contains each component in a proportion of 100 parts by weight of dibucaine, 100–1000 parts by weight of a pharmaceutically acceptable salt of salicyclic acid, 50–500 parts by weight of calcium bromide, and 4–2000 parts of weight of antiphlogistic steroid(s).

8. A method for treating pain according to claim 6 or claim 7, wherein the composition is a liquid having a pH in the range of from 4 to 7.

9. A method for treating pain according to claim 6, wherein the administration is conducted once or twice a week.

10. A method for treating pain according to claim 6, wherein administration is conducted 1 to 4 times in 2 weeks.

11. A method for treating pain according to claim 9 or claim 10, which comprises administration of a composition containing 0.1–25 mg of dibucaine hydrochloride, 0.1–250 mg of a pharmaceutically acceptable salt of salicylic acid, 0.05–125 mg of calcium bromide, and 0.004–500 mg of antiphlogistic steroid(s) per administration at one site.

* * * * *

UNITED STATES PATENT AND TRADEMARK OFFICE
CERTIFICATE OF CORRECTION

PATENT NO. : 5,260,289

DATED : November 9, 1993

INVENTOR(S) : Hyodo et al.

It is certified that error appears in the above-identified patent and that said Letters Patent is hereby corrected as shown below:

ON THE TITLE PAGE:

[57] ABSTRACT:

Line 11, delete "steroid" and substitute therefor -- steroids --.

Column 1, line 57, delete "A" and substitute therefor -- And --;

Column 2, line 36, delete "eircumomarthritis" and substitute therefor -- circumomarthritis --;

Column 2, line 56, delete "preunisolone" and substitute therefor -- prednisolone --;

Column 2, line 63, delete "preunisolone" and substitute therefor -- prednisolone --;

Column 2, line 67, delete "betainethasone" and substitute therefor -- betamethasone --;

UNITED STATES PATENT AND TRADEMARK OFFICE
CERTIFICATE OF CORRECTION

PATENT NO. : 5,260,289

DATED : November 9, 1993

INVENTOR(S) : Hyodo et al.

It is certified that error appears in the above-identified patent and that said Letters Patent is hereby corrected as shown below:

Column 3, line 14, delete "preunisolone" and substitute therefor -- prednisolone --;

Column 4, line 23, delete "preunisolone" and substitute therefor -- prednisolone --;

Column 5, line 21, delete "Increase" and substitute therefor -- increase --;

Signed and Sealed this

Seventeenth Day of January, 1995

Attest:

BRUCE LEHMAN

Attesting Officer

Commissioner of Patents and Trademarks